United States Patent [19]

Rowe et al.

[11] 4,442,051

[45] Apr. 10, 1984

[54] ENCAPSULATION OF INDOMETHACIN

[75] Inventors: James S. Rowe, Twickenham; John E. Carless, Reigate, both of England

[73] Assignee: Nicholas Proprietary Limited, Victoria, Australia

[21] Appl. No.: 330,313

[22] PCT Filed: Apr. 15, 1981

[86] PCT No.: PCT/AU81/00044

§ 371 Date: Dec. 11, 1981

§ 102(e) Date: Dec. 11, 1981

[87] PCT Pub. No.: WO81/02976

PCT Pub. Date: Oct. 29, 1981

[30] Foreign Application Priority Data

Apr. 21, 1980 [GB] United Kingdom ................. 8013003

[51] Int. Cl.³ ............................................. B01J 13/02
[52] U.S. Cl. ...................................... 264/4.3; 424/34; 424/37; 424/262; 428/402.2; 428/402.24

[58] Field of Search .................... 252/316; 424/35, 34; 264/4.3

[56] References Cited

U.S. PATENT DOCUMENTS

| | | | |
|---|---|---|---|
| 3,495,988 | 2/1970 | Balassa | 252/316 X |
| 3,549,555 | 12/1970 | Hiestand et al. | 252/316 |
| 3,557,279 | 1/1971 | Morse | 424/20 |
| 4,010,038 | 3/1977 | Iwasaki et al. | 252/316 X |
| 4,082,688 | 4/1978 | Egawa et al. | 252/316 |

FOREIGN PATENT DOCUMENTS 2146174 3/1972 Fed. Rep. of Germany .

*Primary Examiner*—Richard D. Lovering
*Attorney, Agent, or Firm*—Oblon, Fisher, Spivak, McClelland & Maier

[57] ABSTRACT

Indomethacin is encapsulated by aqueous gelatin/polysaccharide coacervation by first forming a dispersion or paste of Indomethacin in a water-miscible liquid polyhydroxyalkane. Preferably the coacervate system is gelatin/acacia and the polyhydroxyalkane is glycerol.

14 Claims, No Drawings

ENCAPSULATION OF INDOMETHACIN

The present invention relates to the encapsulation of Indomethacin.

It is known to encapsulate particulate material, including drugs, in a coacervate complex by the technique of aqueous complex coacervation in which microcapsules having a core of the particulate material encased in a coating are formed by dispersing the particulate material in an aqueous solution of a pair of colloids of opposite electric charge and then causing a coacervate complex to phase out ("coacervate") of the aqueous solution to enrobe the particulate material. Usually, the colloids employed are gelatin and a polysaccharide, especially acacia (also known as "gum arabic") although other coacervate systems are known and used. The actual coacervation of the complex conveniently is caused by changing the pH of the aqueous solution although other means can be used. The aqueous complex coacervation technique has been used successfully with drugs to provide inter alia protection of the gastro-intestinal tract from irritants.

Indomethacin (i.e. 1-(p-chlorobenzoyl)-5-methoxy-2-methyl-indole-3-acetic acid) is a drug having useful anti-inflammatory, analgesic and antipyretic activity. Unfortunately, it is an irritant to the gastro-intestinal tract and this side-effect has reduced its use. Since it is only sparingly soluble in water and insufficiently wetted to provide a homogeneous dispersion in aqueous solution, attempts to overcome its gastro-intestinal irritancy by encapsulation using aqueous complex coacervation have been unsuccessful. U.S. Pat. No. 3,557,279 describes the preparation of Indomethacin micro-capsules having a gelatin/acacia coating using aqueous complex coacervation and in particular refers to dispersion of the Indomethacin in paraffin oil containing a surfactant. However, the resultant products are not satisfactory. Friable clumps are formed when no paraffin oil is used. When paraffin oil is used, the internal phase of the micro-capsules contains about 37% paraffin oil and micro-capsules of cosiderable size variation (at least 100 to 1500 microns) are formed. In both cases only thin walled micro-capsules are formed.

The Inventors have attempted to improve the wettability of Indomethacin by using ultrasonic vibrations, surface active agents and oils but without success in terms of obtaining a satisfactory encapsulated product. Although a homogeneous dispersion and coacervation was obtained using certain oils, particularly corn oil and arachis oil, the resultant encapsulated Indomethacin had poor flow properties. However, the Inventors have now found that a satisfactory encapsulated product having good flow properties can be obtained if the Indomethacin is mixed with a water-miscible liquid polyhydroxyalkane, such as liquid sorbitol or, especially, glycerol (i.e. 1, 2, 3-trihydroxypropane) to form a dispersion or paste before addition to an aqueous solution for gelatin/polysaccharide complex coacervation. They have found also that the resultant encapsulated product has reduced side-effects compared with currently available Indomethacin preparations.

According to the present invention therefore, there is provided a method of encapsulating Indomethacin comprising mixing Indomethacin with a water-miscible liquid polyhydroxyalkane to form a dispersion or paste, dispersing said dispersion or paste in an aqueous solution of a gelatin/polysaccharide complex coacervate system, causing coacervation of said system to encapsulate the Indomethacin with a coacervate complex, and hardening and dehydrating the resultant microcapsules.

Usually, the Indomethacin will pass through a 200 gauge US sieve size sieve. Preferably the Indomethacin has a 50% weight median diameter in the range 5 to 10 microns with less than 5% w/w of particles greater than 33 microns diameter. It is also preferred that the amount of the Indomethacin present is 15 to 20% by weight of the combined dry weight of the Indomethacin and the coacervate system.

The presently preferred polyhydroxyalkanes for use in the method of the invention are $C_3$–$C_6$ straight chain alkanes having one hydroxy group on each carbon atom of the chain, e.g. liquid sorbitol (i.e. 1, 2, 3, 4, 5, 6-hexahydroxyhexane) or, most preferred, glycerol. The polyhydroxyalkane must be liquid at the temperature at which it is mixed with the Indomethacin and at which the resultant dispersion or paste is dispersed in the aqueous solution, but is not necessarily liquid at ambient temperature. For convenience however, it is preferred that the polyhydroxyalkane is liquid at ambient temperature. The amount of polyhydroxyalkane employed will be sufficient to form a dispersion or paste which will disperse homogeneously in the aqueous solution. Suitably said amount is in the range 2% to 20% by weight, preferably 8 to 12% by weight, of the aqueous coacervation suspension (i.e. the suspension from which the micro-capsules are formed). The optimum amount employed can readily be ascertained by simple experiment.

Essentially conventional aqueous complex coacervation techniques are to be employed for encapsulating the Indomethacin once the dispersion or paste has been formed. Preferably the gelatin is an acid-processed pig skin gelatin having an isoelectric point of 8.5 to 9.5 and the polysaccharide is acacia. Suitably, the dispersion or paste is added to a warm aqueous solution of the polysaccharide or gelatin and then a warm aqueous solution of the gelatin or polysaccharide respectively is added and, after stirring for a few minutes, the pH of the resultant solution is adjusted to, for example, 3.5 to 4.5 to cause coacervation. After stirring, preferably under low shear/high circulation conditions, until the desired amount of encapsulation has occured, the gelatin/polysaccharide wall is hardened by addition of, for example, formalin (i.e. aqueous formaldehyde) or aqueous glutaraldehyde. The optimum coacervation conditions will vary depending upon the constituents employed but can readily be determine by those skilled in the art, if necessary after simple experiment. It is preferred that coacervation conditions are employed to provide microcapsules in the range 30 to 200 microns diameter.

It is advantageous to use a gelatin/polysaccharide ratio of about 1:1 and aqueous gelatin/polysaccharide solutions of 1 to 3% w/v, especially 3% w/v, at 41° to 46° C., especially 46° C. It is also preferred that the pH is in the range 3.8 to 4.0 expecially about 3.9. It is further preferred to cool the hardened coacervate rapidly to a temperature below 10° C., especially below 5° C., and maintain this low temperature first whilst washing with water and subsequently whilst washing with isopropyl alcohol to dehydrate the microcapsules.

According to a particularly preferred embodiment of the invention, a free-flowing particulate Indomethacin product is obtained by a method comprising mixing particulate Indomethacin having a 50% weight median diameter in the range 5 to 10 microns with less than 5% w/w of particles greater than 33 microns diameter with glycerol to form a dispersion or paste, dispersing said dispersion or paste in a 41°–46° C., 1–3%w/v aqueous solution of acacia or acid-processed pig skin gelatin having an isoelectric point of 8.5 to 9.5, stirring into the resultant dispersion a 41°–46° C., 1–3%w/v aqueous solution of said gelatin or acacia respectively, adjusting the pH to 3.8–4.0 to cause coacervation to encapsulate the Indomethacin in a gelatin/acacia coacervate complex, hardening the said complex coating by addition of formaldehyde, rapidly cooling the mixture to below 10° C., maintaining a temperature below 10° C. whilst washing the resultant microcapsules with water and subsequently dehydrating by suspending in isopropanol, and drying the dehydrated microcapsules.

The following Examples illustrate the invention. All percentages are by weight unless otherwise stated.

EXAMPLE 1

Indomethacin (1 g) was triturated with a small quantity of glycerol to form a thin paste which was then thoroughly mixed with a 2% aqueous solution of acacia (250 ml). The dispersion was maintained at 41° C. and stirred at 400 rpm whilst slowly adding a 2% aqueous solution of gelatin (250 ml) also maintained at 41° C. The gelatin solution had previously been allowed to stand for 30 minutes to hydrate the gelatin and then adjusted to pH 3.9 by addition of dilute hydrochloric acid. The Indomethacin and acacia were pharmaceutical grades and the gelatin was acid-processed pig skin gelatin having a Bloom strength of 250 g, an isoelectric point of 9.2 and a viscosity of 7.4 cps (2% gelatin at 25° C.).

The aqueous suspension was stirred at 400 rpm for 5 minutes after addition of the gelatin solution was complete and then the pH adjusted to 3.9. Stirring was continued for a further 40 minutes to allow coacervation and hence encapsulation of the Indomethacin to take place. A 40% formalin solution (10 ml) was then added to harden the capsule walls and stirring continued for a further 5 to 10 minutes. Until this stage the temperature had been maintained at 41° C. but the coacervation vessel was then placed in an ice bath to rapidly cool the mixture to 4° C., at which temperature stirring was stopped and the micro-capsules allowed to settle. The aqueous phase was decanted by drawing off under vacuum and the micro-capsules washed twice with cold isopropanol, air dried and finally dried in a stream of nitrogen gas to yield a free flowing product of Indomethacin particles encapsulated by a hardened gelatin/acacia coacervative complex. This product was suitable for pharmacological use by oral administration and showed reduced gastro-intestinal irritancy compared with uncoated Indomethacin and Indomethacin coated in a sustained release form, believed to be Indomethacin in a plastics matrix.

EXAMPLE 2

The procedure of Example 1 was repeated with the exception that sorbitol was used instead of glycerol. The gelatin/acacia micro-encapsulated product obtained had identical properties to the product of Example 1.

EXAMPLE 3

Indomethacin (15 g) of a mean particle size between 5 and 10 microns was dispersed in glycerol (285 g) and the resultant dispersion was added to an aqueous solution of gelatin (37.5 g in 1212.5 ml) which had previously been warmed to 46° C. and adjusted to pH 3.9. The gelatin was an acid-processed pig skin gelatin with an iso-electric point of 9.0 and a Bloom strength of 250 g. The mixture was stirred for 5 minutes and then added to an aqueous solution of acacia (37.5 g in 1212.5 ml) which had also previously been warmed to 46° C. and adjusted to pH 3.9. Stirring was continued for a further 5 minutes and then the pH adjusted to 3.9 by addition of 0.1 M hydrochloric acid. Stirring was continued for a further 40 minutes at 46° C. and pH 3.9, aqueous formaldehyde (75 ml 36% solution) was added and the stirring continued for a further 5 minutes. The mixture was subsequently rapidly cooled to about 5° C. whilst stirring and then the micro-capsules allowed to settle during a period of 30 minutes at about 5° C. The micro-capsules were filtered off until the surface water had been removed and then resuspended in water. This filtering and resuspending procedure was repeated several times to reduce the glycerol content to about 0.5% by weight. The micro-capsules were then spray dried from aqueous suspension in a conventional spray drier.

All the stirring referred to above was conducted in such a manner as to provide low shear but high circulation.

The micro-encapsulated Indomethacin obtained in this Example contained 16.67% by weight Indomethacin, 41.67% by weight acacia and 41.67% by weight gelatin and was a free flowing powder. All of the product passed through a 250 micron sieve. The time taken for 50% of the Indomethacin to dissolve in water at pH 6.8 was about 7 minutes.

EXAMPLE 4

Indomethacin B.P. 1980 (45.0 g) was passed through a hammer mill fitted with a 0.5 mm screen and then dispersed in glycerol Ph. Eur. 1975 (855.0 g) at room temperature. The dispersion was added to a solution of acid-processed pig skin gelatin B.P. 1980 (112.5 g) in distilled water (3.6375L), which solution had been adjusted to pH 3.9 with hydrochloric acid and subsequently warmed to 46° C. The resultant Indomethacin/glycerol/gelatin dispersion was then added to a solution of spray-dried acacia Ph. Eur. 1969 (112.5 g) in distilled water (3.6375L), which solution also had been adjusted to pH 3.9 with hydrochloric acid and subsequently warmed to 46° C. The pH of the resultant coacervation mixture was adjusted to 3.9 with hydrochloric acid and maintained at 46° C. and pH 3.9 for 40 minutes whilst continuing to stir. Formaldehyde solution B.P. (225 ml) was then added, and stirring continued for a further 5 minutes and then the mixture was cooled rapidly to 10° C. whilst stirring.

The microcapsules were filtered off from the cooled mixture, resuspended in cold distilled water, filtered off again and resuspended in cold isopropyl alcohol (3L) for 20 minutes before being air dried at room temperature until free flowing. The microcapsules were further dried at 50° C., sieved through a 250 micron screen and allowed to equilibrate at room temperature for 48 hours to provide a pale cream free flowing powder (yield 253 g).

The powder product consisted of discrete, opaque, spherical or near spherical particles (microcapsules) and small agglomerates of such particles, said agglomerates having an open, not densely packed, structure. Fibres and non-spherical particles were substantially absent. On adding a drop of distilled water, the outer zone of each particle cleared to give a transparent layer and each particle revealed a white granular inclusion or inclusions of Indomethacin. The hydrated particles maintained their integrity, did not spread when in contact with a glass surface and did not coalesce when in contact with one another. The Indomethacin content was 16.67% w/w with respect to the dry weight of the particles. The time taken for 50% of the total Indomethacin content of the microcapsules to dissolve in water at pH 6.8 was 3.98 minutes and 90% dissolved in 9.87 minutes.

BIOAVAILABILITY

Bioavailability cross-over studies in healthy adult male humans using gelatin capsules containing 25 mg Indomethacin in the form of the microcapsules of Example 4 showed no significant differences in bioavailability compared with gelatin capsules containing 25 mg of micronized non-encapsulated Indomethacin (which latter capsules are available in the United Kingdom under the Registered Trade Mark INDOCID). Comparison with a sustained release 75 mg Indomethacin capsule (available in the United Kingdom under the Registered Trade Mark INDOCID R and apparently comprising of micronized Indomethacin dispersed in an insoluble matrix) by a cross-over study in healthy adult male humans indicates that the microcapsules of Example 4 do not have sustained release characteristics.

ARTHRITIC PATIENT TOLERANCE

Tolerance, frequency and severity of side effects associated with the oral administration of three formulations of Indomethacin were evaluated in 50 patients with arthritic disorders. The formulations were:

A. Gelatin capsules containing 25 mg Indomethacin in the form of the microcapsules of Example 4;

B. Commercially available (INDOCID) gelatin capsules containing 25 mg of micronized non-encapsulated Indomethacin; and C. Commercially available (INDOCID R) sustained-release capsules containing 75 mg Indomethacin.

In a single dose study patients were randomly assigned to one of the following formulation dosage levels and then crossed-over to another regimen with at least 3 consecutive days inbetween.

| | |
|---|---|
| 2 × A | (50 mg) |
| 3 × A | (75 mg) |
| 4 × A | (100 mg) |
| 2 × B | (50 mg) |
| 3 × B | (75 mg) |
| 4 × B | (100 mg) |
| 1 × C | (75 mg) |

In a multiple dose study patients received repeat doses ranging from 50–100 mg/day, of A and B for a period of 5 days, and C at a dose of 75 mg per day for a period of 5 days, on a cross-over basis.

In both studies, the patients were monitored routinely by the Medical and Nursing Staff. All relevant comments made by the Patients were recorded and any side effects, whether spontaneously volunteered or clinically evident were recorded on the appropriate record form. A standard questionnaire was completed which avoided direct questioning to elicit untoward results. The questionnaire asked "How did you find the capsules"? If the response implied the occurrence of an untoward effect this was graded according to a Verbal Score Scale, and the Patient was asked to complete a Visual Analogue Scale (10 cm line) demarcated at either end by the extremes of the subjective assessment of the side effect.

The results obtained are given below; the abbreviations CNS and G.I. represent central nervous system and gastrointestinal respectively.

TABLE 1

Single Dose Study
Patients exhibiting side effects, out of 50 studied:

| Formulation | Dose | CNS Side Effects | G.I. Side Effects |
|---|---|---|---|
| A | 50 mg | 15 | 5 |
| A | 75 mg | 26 | 6 |
| A | 100 mg | 22 | 9 |
| B | 50 mg | 18 | 9 |
| B | 75 mg | 32 | 11 |
| B | 100 mg | 25 | 17 |
| C | 75 mg | 21 | 9, 20 & 18* |

*C was given on a cross-over basis in comparison with 50 mg doses of indomethacin, 75 gm and 100 mg doses. Three figures are, therefore given under the GI. side effects for C relating to 50, 75 and 100 mg of the other Indomethacin formulation studies.

Multiple Dose Study

Of 50 patients in the multiple doses phase cross-over study on the three formulations, 32 patients exhibited side effects of varying severity on one or more of the formulations. The results are summarised in the following Table 2 indicating the severity of the side effect as mild (Scale 1–2), moderate (Scale 4) or severe (Scale 4–5)

TABLE 2

Number of Patients exhibiting side effects out of 50 studied:

| Side Effect | A | B | C |
|---|---|---|---|
| Mild CNS | 1 | 7 | 10 |
| Moderate CNS | 4 | 8 | 5 |
| Severe CNS | 5 | 10 | 6 |
| Mild G.I. | 2 | 4 | 4 |
| Moderate G.I. | 1 | 4 | 5 |
| Severe G.I. | 3 | 5 | 9 |
| CNS and/or G.I. | 12 | 30 | 26 |

It will be noted from Table 2 that of the 32 patients exhibiting side effects only 12 exhibited side effects on A compared with 26 on C and 30 on B. Of the 10 patients exhibiting CNS side effects on A, all exhibited at least the same severity of side effects on one or both of B and C with 7 exhibiting at least the same severity of side effects on both B and C. Of the 6 patients exhibiting G.I. side effects on A, all exhibited at least the same severity of side effects on one or both of B and C with 5 exhibiting at least the same severity of side effects on both B and C.

The results of the single and multiple dose studies reported above clearly indicate that the encapsulation of Indomethacin by the method of the present invention significantly reduces the incidence of side effects, especially gastrointestinal side effects, usually associated with Indomethacin.

We claim:

1. A method of encapsulating Indomethacin comprising mixing Indomethacin with a water-miscible liquid polyhydroxyalkane to form a dispersion or paste, dispersing said dispersion or paste in an aqueous solution of a gelatin/polysaccharide coacervate system, causing coacervation of said system to encapsulate Indomethacin with a coacervate complex, and hardening and dehydrating the resultant microcapsules.

2. A method as claimed in claim 1 wherein the polysaccharide is acacia, and the gelatin is an acid-processed pig skin gelatin having an isoelectric point of 8.5–9.5.

3. A method as claimed in claim 1 wherein the Indomethacin has a 50% weight median particle diameter in the range 5 to 10 microns with less than 5% w/w of particles greater than 33 microns diameter.

4. A method as claimed in claim 1 wherein Indomethacin is present in an amount in the range 15 to 20% by weight of the combined dry weight of the coacervate system and Indomethacin.

5. A method as claimed in claim 1 wherein the polyhydroxyalkane is a $C_3$–$C_6$ straight chain alkane with one hydroxy group on each carbon atom of the chain.

6. A method as claimed in claim 1 wherein the polyhydroxyalkane is glycerol.

7. A method as claimed in claim 1 wherein the gelatin and polysaccharide are used as 1–3% w/v solutions, and the coacervation is carried out at 41°–46° C., and at a pH in the range 3.8 to 4.0.

8. A method as claimed in claim 7 wherein said solutions are 3% w/v, the temperature is 46° C. and the pH is about 3.9.

9. A method as claimed in claim 1 wherein the coacervate coating is hardened by treatment with aqueous formaldehyde solution.

10. A method as claimed in claim 1 wherein the amount of polyhydroxyalkane used constitutes 2 to 20% by weight of the aqueous coacervation suspension.

11. A method as claimed in claim 1 wherein the dehydration is carried out by suspending the microcapsules in a dehydrating agent and subsequently drying the dehydrated microcapsules.

12. A method as claimed in claim 11 wherein the dehydrating agent is isopropanol.

13. A method of preparing a free flowing particulate Indomethacin product wherein particulate Indomethacin having a 50% weight median particle diameter in the range 5 to 10 microns with less than 5% w/w of particles greater than 33 microns diameter is mixed with glycerol to form a dispersion or paste; said dispersion or paste is dispersed in a 41° to 46° C., 1–3% w/v aqueous solution of acacia or acid-processed pig skin gelatin having an isoelectric point of 8.5–9.5; the resultant dispersion is stirred into a 41° to 46° C., 1–3% w/v aqueous solution of said gelatin or acacia respectively; the pH is adjusted to pH 3.8 to 4.0 to cause coacervation to encapsulate the Indomethacin in a gelatin/acacia coacervate complex; the said complex coating is hardened by addition of formaldehyde, rapidly cooling the mixture to below 10° C., maintaining a temperature below 10° C. whilst washing the resultant microcapsules with water and subsequently dehydrating them by suspending in isopropanol, and drying the dehydrated microcapsules.

14. A method as claimed in claim 13 wherein said aqueous solutions are 3% w/v and at 46° C., and the pH is adjusted to about 3.9.

* * * * *